United States Patent [19]

Emmett et al.

[11] Patent Number: 4,632,924

[45] Date of Patent: Dec. 30, 1986

[54] 5-(4-SUBSTITUTED)PHENYL-2-PYRAZI-NONES

[75] Inventors: John C. Emmett, Welwyn; Robert A. Slater, Letchworth, both of England

[73] Assignee: SmithKline Beckman Corporation, Philadelphia, Pa.

[21] Appl. No.: 677,006

[22] Filed: Nov. 30, 1984

[30] Foreign Application Priority Data

Dec. 2, 1983 [GB] United Kingdom ............... 8332313

[51] Int. Cl.⁴ ................ C07D 241/08; A61K 31/495
[52] U.S. Cl. ..................................... 514/255; 544/408
[58] Field of Search ....................... 544/408; 514/255

[56] References Cited

U.S. PATENT DOCUMENTS

| | | | |
|---|---|---|---|
| 3,745,161 | 7/1973 | Tsung-Ying et al. | 544/406 |
| 4,423,045 | 12/1983 | Brown et al. | 514/222 |
| 4,489,074 | 12/1984 | Brown et al. | 514/222 |
| 4,514,568 | 4/1985 | Coates | 544/408 |

FOREIGN PATENT DOCUMENTS

| | | | |
|---|---|---|---|
| 86301 | 8/1983 | European Pat. Off. | |
| 96517 | 12/1983 | European Pat. Off. | 544/408 |
| 146282 | 6/1985 | European Pat. Off. | 514/255 |
| 59-144772 | 8/1984 | Japan | 544/408 |

OTHER PUBLICATIONS

McOmie, ed., *Protective Groups in Organic Chemistry*, Plenum Press, New York, 1973, pp. 46–61.
Sheradsky et al., *J.C.S. Perkin I:*1296–1299 (1977).
Ohta et al., Hukusokan Kagaku Toronkai Kuen Yoshishu 8th:84–88 (1975), (Chem. Abstr. 84:164, 723Y).
Greene, ed., Protective Groups in Organic Synthesis, John Wiley and Sons, New York, 1981, pp. 222–249.

*Primary Examiner*—Donald G. Daus
*Assistant Examiner*—William A. Teoli, Jr.
*Attorney, Agent, or Firm*—Mark R. Daniel; Janice E. Williams; Alan D. Lourie

[57] ABSTRACT

This invention relates to 5-(4-substituted)phenylpyrazinone compounds which have positive inotropic and vasodilator activity. One such compound is 5-(4-carboxamidophenyl)pyrazin-2(1H)-one.

10 Claims, No Drawings

5-(4-SUBSTITUTED)PHENYL-2-PYRAZINONES

The present invention relates to pyrazinone derivatives and in particular to such compounds having a substituted phenyl group at the 5-position of the pyrazinone ring. The invention further relates to processes for their preparation, their use as medicaments and to pharmaceutical compositions containing them.

Accordingly the present invention provides compounds of the formula (I):

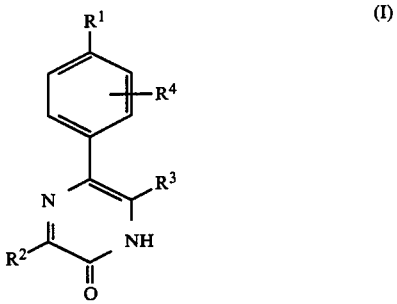

and pharmaceutically acceptable salts thereof, wherein:
$R^1$ is cyano; a group —$COR^5$ wherein $R^5$ is hydrogen, $C_{1-6}$alkyl or $C_{1-6}$alkoxy; or $R^1$ is a group —$CONR^6R^7$ wherein $R^6$ and $R^7$ are independently hydrogen, $C_{1-6}$alkyl or benzyl; and
$R^2$, $R^3$ and $R^4$ are independently hydrogen or $C_{1-4}$alkyl.

Suitably $R^2$ is $C_{1-4}$alkyl for example methyl, ethyl, n-propyl or iso-propyl. Preferably $R^2$ is hydrogen.

Suitably $R^3$ is $C_{1-4}$ alkyl for example methyl. Preferably $R^3$ is hydrogen.

Suitably $R^4$ is $C_{1-4}$alkyl for example methyl. Preferably $R^4$ is hydrogen.

Thus in a preferred aspect of the compounds of the formula (I), $R^2$, $R^3$ and $R^4$ are simultaneously hydrogen.

Suitably $R^1$ is a group —$COR^5$ as hereinbefore defined. For example $R^1$ may be $C_{1-7}$alkanoyl for example formyl, acetyl or propionyl, or $C_{1-6}$alkoxycarbonyl for example methoxycarbonyl, ethoxycarbonyl, propoxycarbonyl or butoxycarbonyl.

In an alternative aspect $R^1$ is a group —$CONR^6R^7$ as hereinbefore defined. For example $R^1$ may be carboxamido, $C_{1-6}$alkylcarbamoyl for example methylcarbamoyl or ethylcarbamoyl, di-($C_{1-6}$)alkylcarbamoyl for example dimethylcarbamoyl, diethylcarbamoyl or di-propylcarbamoyl, or di-benzylcarbamoyl.

More suitably $R^1$ is cyano, carboxamido, $C_{1-6}$alkylcarbamoyl, di($C_{1-6}$)alkylcarbamoyl or $C_{1-6}$alkoxycarbonyl.

Preferably $R^1$ is cyano, carboxamido, methoxycarbonyl or dimethylcarbamoyl. Of these cyano and carboxamido are most preferred.

Specific compounds of this invention include:
5-[4-(N,N-dimethylcarboxamido)phenyl]pyrazin-2(1H)-one,
5-(4-methoxycarbonylphenyl)pyrazin-2(1H)-one,
5-(4-cyanophenyl)pyrazin-2(1H)-one and
5-(4-carboxamidophenyl)pyrazin-2(1H)-one.

The compounds of this invention are depicted as 2(1H)-pyrazinones but of course the present invention covers all tautomeric forms thereof.

The compounds of the formula (I) may form salts, for example with a metal ion such as an alkali metal for example sodium or potassium.

In order to use a compound of the formula (I) or a pharmaceutically acceptable salt thereof for the treatment of mammals including humans it is normally formulated in accordance with standard pharmaceutical practice as a pharmaceutical composition.

Compounds of formula (I) and their pharmaceutically acceptable salts may be administered orally, parenterally, trans-dermally or rectally.

Compounds of formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose.

Typical parenteral compositions consist of a solution or suspension of the compound or salt in a sterile aqueous carrier or parenterally acceptable oil.

A typical suppository formulation comprises a compound of formula (I) or a pharmaceutically acceptable salt thereof which is active when administered in this way, with a binding and/or lubricating agent for example gelatin or cocoa-butter or other low melting vegetable waxes or fats.

Preferably the composition is in unit dosage form for example a tablet or capsule so that the patient may administer to himself a single dose.

Each dosage unit contains preferably from 5 to 250 mg of a compound of formula (I) or a pharmaceutically acceptable salt thereof calculated as the free base.

The daily dosage regimen for an adult human patient is from about 5 mg to about 1500 mg of the compound of formula (I) or a pharmaceutically acceptable salt thereof calculated as the free base. The active ingredient may be administered from 1 to 6 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure.

The compounds of formula (I) and their pharmaceutically acceptable salts are tested for cardiac stimulant activity following a procedure based on that of S. C. Verma and J. H. McNeill (J.Pharm & Exp. Therapeutics, 200, 352-362 (1977)). Guinea pigs (500-700 g) of either sex are sacrificed and the hearts are quickly removed and transferred to a dissecting dish containing oxygenated bathing fluid. While in the bathing medium, the right ventricle is cut into two strips. The strips are each suspended in a 75 ml bath containing Krebs Henseleit solution at 37° C., and the bath is bubbled with 95% oxygen and 5% carbon dioxide. The ventricular strips are electrically stimulated at a frequency of 0.5 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested gave a 50% increase in the force of contraction of the ventricular strips at concentrations in the bathing fluid of less than $10^{-4}$ molar, thus showing that they have activity as positive inotropic agents. The compounds of Examples 1 and 2, according to the above test method, gave $EC_{50}$ values of below 20 μM. Amrinone (5-amino-3,4'-bipyrid-6(1H)-one), a known compound of interest in this therapeutic category gives an $EC_{50}$ value of 15 μm.

The compounds of this invention may be co-administered with other pharmaceutically active compounds. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

In another aspect the present invention provides a process for preparing a compound of the formula (I) or a pharmaceutically acceptable salt thereof, which process comprises:

(a) reacting a compound of the formula (II) with a source of cyanide:

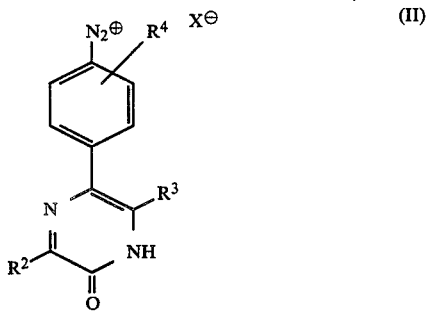

wherein $R^2$, $R^3$ and $R^4$ are as hereinbefore defined, and $X^-$ is a counter-ion, and for preparing a compound of the formula (I) wherein $R^1$ is other than cyano, converting cyano to another group $R^1$; or (b) reacting a compound of the formula (III):

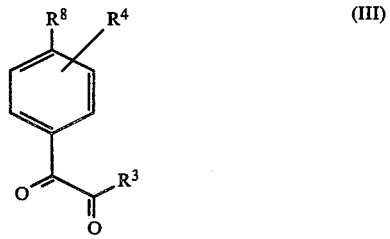

wherein $R^3$ and $R^4$ are as hereinbefore defined, and $R^8$ is a group $R^1$ or a protected derivative thereof, with a compound of the formula (IV):

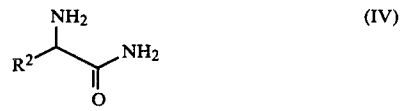

wherein $R^2$ is as hereinbefore defined;
and optionally thereafter:
(i) removing any protecting group,
(ii) forming a pharmaceutically acceptable salt.

The reaction between a compound of the formula (II) and a source of cyanide is conveniently performed in conventional manner, for example in a substantially aqueous medium at an elevated temperature between 50° C. and 100° C. The source of cyanide is conveniently a cyanide salt formed with a metal ion for example an alkali metal such as sodium or potassium, or copper or a mixture of such salts.

The compounds of the formula (II) may be prepared by diazotising a compound of the formula (V):

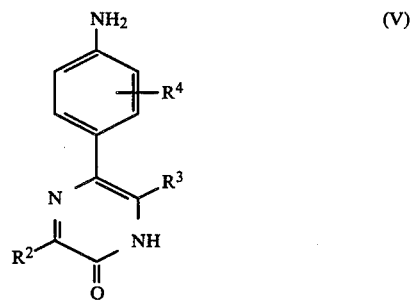

wherein $R^2$, $R^3$ and $R^4$ are as hereinbefore defined.

Such diazotisation may be performed under conventional conditions, for example at low temperatures between about −20° C. and +10° C., preferably about 0° C., in the presence of concentrated acid and nitrite ion.

The compound of the formula (V) wherein $R^2$–$R^4$ are independently hydrogen is described by Sheradsky et al. J. Chem. Soc. 1977 p1296. The other compounds of the formula (V) can be prepared in a similar manner.

The compounds of the formula (I) wherein $R^1$ is carboxamido may be prepared by the hydrolysis of a corresponding compound wherein $R^1$ is cyano. Conveniently such hydrolysis is performed in concentrated mineral acid, for example sulphuric acid, and conveniently is performed at an elevated temperatures, for example between ambient and 100° C., preferably between 40° and 70° C.

Compounds of the formula (I) wherein $R^1$ is $C_{1-6}$-alkoxycarbonyl or a group —$CONR^6R^7$ may be prepared by reacting a corresponding compound wherein $R^1$ is carboxy or an activated derivative thereof with a $C_{1-6}$alkanol or an amine of the formula $NHR^6R^7$. In addition compounds of the formula (I) wherein $R^1$ is a group —$CONR^6R^7$ may be prepared from compounds wherein $R^1$ is $C_{1-6}$alkoxycarbonyl by reaction with an amine $NHR^6R^7$.

The reaction between the compounds of the formulae (III) and (IV) in general is performed under basic conditions, and is conveniently performed in solution in an aqueous $C_{1-4}$alkanol.

Conveniently $R^8$ is a group $R^1$ as hereinbefore defined. In an alternative $R^8$ is a protected derivative of a group $R^1$, for example a protected aldehyde or ketone. In addition $R^8$ can be a carboxy group protected by a group that is removable on acidic or basic hydrolysis, hydrogenolysis or by enzymatic hydrolysis; subsequently said carboxy group can be converted to a group $R^1$.

Pharmaceutically acceptable salts of the compounds of the formula (I) may be prepared in conventional manner.

The following Descriptions and Examples serve to illustrate this invention.

DESCRIPTIONS

Description 1

5-(4-Aminophenyl)-3-methyl-2(1H)-pyrazinone hydrobromide (a) To a stirred suspension of sodium hydride (2.1 g, 50% in oil) in dry dimethylformamide (35 ml) with external cooling was added portionwise, benzyl N-hydroxy-N-phenylcarbamate (10.6 g). After 5 minutes a brown solution was obtained to which was added 2-chloro-3-methylpyrazine (5.5 g) and the mixture was allowed to attain room temperature. The solution was poured into water (200 ml) and the aqueous phase decanted from the dark oil. The aqueous solution deposited a yellow solid which was collected and washed with ethanol to give 5-(4-benzyloxycarbonylaminophenyl)-3-methyl-2(1H)-pyrazinone (1.55 g. m.p. 238°-240° C.).

(b) 5-(4-Benzyloxycarbonylaminophenyl)-3-methyl-2(1H)-pyrazinone (1.5 g) was treated with hydrogen bromide in acetic acid in a manner similar to that described in Description 3 to give the title compound as its hydrobromide salt (1.09 g) which on recrystallisation from ethanol/ether had m.p.>300° C.; $\nu$(Nujol mull) 1632, 1640 cm$^{-1}$.

Description 2

5-(4-Aminophenyl)-6-methyl-2(1H)-pyrazinone hydrobromide (a) 2-Chloro-6-methylpyrazine (2.0 g) was treated with benzyl N-hydroxy-N-phenylcarbamate (3.7 g) in a manner similar to that described in Description 1 to give 5-(4-benzyloxycarbonylaminophenyl)-6-methyl-2(1H)-pyrazinone (0.52 g) which on recrystallisation from ethanol had m.p. 232° C.

(b) 5-(4-Benzyloxycarbonylaminophenyl)-6-methyl-2(1H)-pyrazinone (0.5 g) was treated with hydrogen bromide in acetic acid in a manner similar to that described in Description 3 to give the title compound as its hydrobromide salt (340 mg) which after digestion with hot ethanol had m.p.>300° C.; $\delta$(D$_2$O) inter alia 2.39 (3H, d, CH$_3$), 8.03 (1H, q, pyrazinone ring 3-H); $\nu$(KBr) 1705, 1750 cm$^{-1}$.

Description 3

5-(4-Aminophenyl)-2-(1H)-pyrazinone (a) A solution of benzyl N-hydroxy-N-phenylcarbamate (8.0 g) in ethanolic potassium hydroxide (0.27N; 120 ml) was treated with chloropyrazine (4.18 g) and molecular sieve (0.5 g). The mixture was stirred for 2 hours at room temperature and then allowed to stand for 4 days. Evaporation of the reaction mixture under reduced pressure gave an orange residue which was suspended in dilute acetic acid, filtered off, and heated in hot 1-propanol (about 200 ml). On cooling, the resulting solution gave a golden precipitate of 5-(4-benzyloxycarbonylaminophenyl)-2(1H)-pyrazinone m.p. 240°-244° C.

(b) A solution of 5-(4-benzyloxycarbonylaminophenyl)-2(1H)-pyrazinone (1.1 g) in 15% w/v hydrogen bromide in acetic acid solution (30 ml) was refluxed for 30 min. The yellow precipitate which formed was filtered off and it was washed with a little 1-propanol and then recrystallised from ethanol-water containing 2 drops of concentrated hydrobromic acid to give 5-(4-aminophenyl)-2(1H)-pyrazinone hydrobromide (1.03 g m.p.>300° C.). This is converted to 5-(4-aminophenyl)-2(1H)-pyrazinone by neutralising.

Description 4

5-(4-Carboxyphenyl)pyrazin-2(1H)-one 5-(4-Cyanophenyl)pyrazin-2(1H)-one (1.0 g) was dissolved in aqueous 2N NaOH and the solution was refluxed for 2 hours. The solution was then acidified with concentrated hydrochloric acid and the resultant precipitate collected by filtration and washed with acetone. This solid was dissolved in dilute sodium bicarbonate solution, which was treated with charcoal and acidified to pH 3. The resultant precipitate was collected washed with with water and dried to give the title compound as a cream-coloured solid (1.2 g); m.p.>300° C.; $\delta$(DMSO-d$_6$) 7.99 (s, aromatic protons), 8.15 (s, pyrazinone protons); $\nu$max (liquid paraffin mull) 1710, 1665, 1608, 865 cm$^{-1}$.

EXAMPLE 1

5-(4-Cyanophenyl)pyrazin-2(1H)-one 5-(4-Aminophenyl)pyrazin-2(1H)-one (14.0 g) was dissolved in a mixture of water (70 ml) and concentrated hydrochloric acid (10 ml) and chilled to 0° C. To this was added over 10 minutes a solution of sodium nitrite (4.5 g) in water (40 ml), also chilled to 0° C. The resultant mixture was stirred at 0° C. for a further 10 minutes and subsequently was added over 10 minutes to a solution of cuprous cyanide (14.0 g) and sodium cyanide (17.6 g) in water (250 ml), the reaction mixture being maintained at 60° C. Extensive frothing occurred. The temperature of the reaction mixture was raised to about 100° C. and stirring continued at this temperature for a further 15 minutes. The reaction mixture was allowed to cool, and the dark precipitate was collected by filtration and dried in air to afford a solid (10.0 g).

A small batch of this solid (3.0 g) was recrystallised from dimethylsulphoxide/water (25/100 ml), giving a buff solid which was dried under vacuum at 70° C. to afford the title compound (1.4 g); m.p.>300° C.; $\nu$max (liquid paraffin mull) 2225, 1696, 1665 cm$^{-1}$; $\delta$(DMSO-d$_6$) 7.84 (2H, m, aromatic protons), 8.06 (2H, m, aromatic protons), 8.1 (2H, broad, s, pyrazinone protons).

EXAMPLE 2

5-(4-Carboxamidophenyl)pyrazin-2(1H)-one 5-(4-Cyanophenyl)pyrazin-2(1H)-one (1.0 g) was dissolved in concentrated sulphuric acid (10 ml), stirred at 55° C. for 20 minutes, then poured on to ice-water (100 ml). The resultant precipitate was collected by filtration and recrystallised from dimethylformamide/water. The mother liquor from this recrystallisation was taken, evaporated under reduced pressure and dried under vacuum at 70° C. to afford the title compound as a solid (0.6 g); m.p.>300° C.; $\nu$max (KBr disc) 1660, 1610 cm$^{-1}$; δ(DMSO-d$_6$) 7.96 (s, aromatic protons), 8.16 (s, pyrazinone protons).

EXAMPLE 3

5-(4-Methoxycarbonylphenyl)pyrazin-2(1H)-one

A mixture of 5-(4-carboxyphenyl)pyrazin-2(1H)-one (1.2 g) and anhydrous methanol was stirred with heating under reflux while a gentle steam of dry hydrogen chloride gas was passed through the solution. After two hours the solvent was evaporated under reduced pressure and the residue was purified by elution from a silica gel column with chloroform/methanol mixtures followed by crystallisation from methanol. This afforded the title compound as a crystalline solid (0.8 g); m.p. 240°–242° C.

EXAMPLE 4

5-[4-(N,N-Dimethylcarboxamido)phenyl]pyrazin-2(1H)-one 5-(4-Methoxycarbonylphenyl)pyrazin-2(1H)-one (1.0 g) and a solution of dimethylamine in ethanol (33%; 100 ml) were heated under reflux for 72 hours to give the title compound.

What is claimed is:

1. A compound of the formula (I):

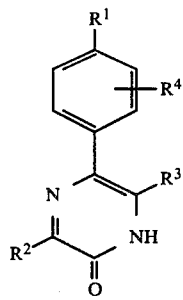

or a pharmaceutically acceptable salt thereof, wherein:
R$^1$ is cyano; a group —COR$^5$ wherein R$^5$ is hydrogen, C$_{1-6}$alkyl or C$_{1-6}$alkoxy; or R$^1$ is a group —CONR$^6$R$^7$ wherein R$^6$ and R$^7$ are independently hydrogen, C$_{1-6}$alkyl or benzyl; and
R$^2$, R$^3$ and R$^4$ are independently hydrogen or C$_{1-4}$alkyl.

2. A compound according to claim 1 wherein R$^2$, R$^3$ and R$^4$ are simultaneously hydrogen.

3. A compound according to either claim 1 or 2 wherein R$^1$ is a group —COR$^5$.

4. A compound according to either claim 1 or 2 wherein R$^1$ is a group —CONR$^6$R$^7$.

5. A compound according to either claim 1 or 2 wherein R$^1$ is cyano, methoxycarbonyl, carbamoyl or dimethylcarbamoyl.

6. A compound according to claim 1 which is: 5-(4-cyanophenyl)pyrazin-2(1H)-one, or 5-(4-carboxamidophenyl)pyrazin-2(1H)-one.

7. A pharmaceutical composition for treating cardiovascular disease in a mammal in need thereof which comprises a compound according to claim 1 and a pharmaceutically acceptable carrier therefor.

8. A pharmaceutical composition for treating cardiovascular disease in a mammal in need thereof which comprises a compound according to claim 6 and a pharmaceutically acceptable carrier therefor.

9. A method for treating cardiac disease in a mammal comprising administering an effective dose of a compound of claim 1.

10. A method for stimulating cardiac activity in a mammal comprising administering an effective dose of a compound of claim 1.

* * * * *

UNITED STATES PATENT AND TRADEMARK OFFICE
CERTIFICATE OF CORRECTION

PATENT NO. : 4,632,924

DATED : December 30, 1986

INVENTOR(S) : John C. Emmett et al.

It is certified that error appears in the above-identified patent and that said Letters Patent is hereby corrected as shown below:

On the Title Page:

ASSIGNEE: Smith Kline & French Laboratories Ltd.
Welwyn Garden City, England

STATE OF INCORPORATION: Great Britain

Signed and Sealed this

Seventh Day of April, 1987

Attest:

DONALD J. QUIGG

*Attesting Officer*  *Commissioner of Patents and Trademarks*